US007056864B2

(12) United States Patent
Rosskopf et al.

(10) Patent No.: US 7,056,864 B2
(45) Date of Patent: Jun. 6, 2006

(54) METHODS OF REDUCING PESTS BY USE OF HALOGEN SUBSTITUTED ETHANOL

(75) Inventors: Erin Nichole Rosskopf, Fort Pierce, FL (US); William H. Basinger, Hiram, GA (US); Husein Ahmad-Mousa Ajwa, Salinas, CA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 320 days.

(21) Appl. No.: 10/462,912

(22) Filed: Jun. 17, 2003

(65) Prior Publication Data

US 2004/0038828 A1    Feb. 26, 2004

Related U.S. Application Data

(60) Provisional application No. 60/395,230, filed on Jul. 11, 2002.

(51) Int. Cl.
*A01N 31/02*    (2006.01)
*A01P 5/00*    (2006.01)
*A01P 7/04*    (2006.01)
*A01P 13/00*    (2006.01)

(52) U.S. Cl. ..................... 504/356; 514/724
(58) Field of Classification Search ............. 504/353, 504/356; 514/724
See application file for complete search history.

(56) References Cited

U.S. PATENT DOCUMENTS

| 4,016,186 | A | 4/1977 | Kondo et al. |
| 4,253,921 | A | 3/1981 | Baldwin et al. |
| 4,726,144 | A | 2/1988 | Young et al. .................. 47/58 |
| 5,447,945 | A | 9/1995 | Sutter et al. ................ 514/373 |
| 5,753,183 | A | 5/1998 | Ohr et al. ...................... 422/37 |

FOREIGN PATENT DOCUMENTS

JP    2000-136107    *  5/2000

OTHER PUBLICATIONS

Derwent Abstract 1967-02610H of DD 60177A. 1968.*
JPAB Abstract of JP 2000-136107, May 2000.*

(Continued)

*Primary Examiner*—S. Mark Clardy
(74) *Attorney, Agent, or Firm*—John D. Fado; G. Byron Stover (57) ABSTRACT

A method for reducing pests in an object or area by applying to the object or area a pest reducing effective amount of halogen substituted ethanol (e.g., 2-iodoethanol, 2-bromoethanol, or mixtures thereof). The pests may be, for example, fungi, insects, nematodes, bacteria, weeds, or mixtures thereof. The object or area may be, for example, soil, structures, agricultural commodities, plants, or mixtures thereof.

29 Claims, 11 Drawing Sheets

2-Bromoethanol (AJMC-330) *Fusarium* Tetrazolium Assay.
y = 0.2088/(1+ 0.0064x) Adj. Rsqr=0.95.

OTHER PUBLICATIONS

Ajwa, H., and T. Trout, Strawberry growth and yield with three years of drip fumigation, 2000 Annual International Research Conference on Methyl Bromide Alternatives and Emissions Reductions, Orlando, FL, Abstract 25.

Ajwa, H., T. Trout, S.D. Nelson, and M. Schutter, Drip fumigation: water and fumigant distribution in soil, 2001 Annual International Research Conference on Methyl Bromide Alternatives and Emissions Reductions, San Diego, CA, Abstract 50.

Mace, M. E., et al., "A Rapid, Tetrazolium-Based Assay for Toxicity of the Phytoalexin Desoxyhemigossypol to *Verticillium dahliae*", *Pesticide Biochemistry and Physiology*, vol. 38, pp. 57-59 (1990).

U.S. EPA, Methyl Bromide Phase Out Web Site, pp. 1-18, last updated Nov. 29, 2000.

* cited by examiner

2-Bromoethanol (AJMC-330) *Fusarium* Tetrazolium Assay.
y = 0.2088/(1+ 0.0064x) Adj. Rsqr=0.95.

Fig. 1

AJMC # 334
Fusarium Tetrazolium Assay

2-Iodoethanol (AJMC-334) *Fusarium* Tetrazolium Assay.
y = (0.2346+0.0003x)/(1+0.0452x)  Adj Rsqr = 0.99

Fig. 2

Benlate *Fusarium* Tetrazolium Assay.
y = 0.2181/(1+0.0673x)  Adj Rsqr = 0.96

Fig. 3

2-Bromoethanol (AJMC-330) Nutsedge Greenhouse Assay.
$y = 4.42/(1+(x/525)^{11.53})$  Adj Rsqr = 0.84

Fig. 4

2-Iodoethanol (AJMC-334) Nutsedge Greenhouse Assay.
y=(4.6666-0.0040x)/(1+0.0021x) Adj Rsqr = 0.95

Fig. 5

2-Bromoethanol (AJMC-330) Barnyard Assay.
y=(9.67-0.033x-0.0002x^2)/(1+0.3572x + 0.0036x^2) Adj Rsqr = 0.83

Fig. 6

2-Bromoethanol (AJMC-330) Pigweed Assay.
Y = (17.67 + 7.21x −0.09x^2 - 0.0002x^3)/(1 + 1.9x +0.0081x^2)
Adj Rsqr = 0.99

Fig. 7

2-Iodoethanol (AJMC-334) Barnyard Grass Assay.
y=14.0/(1+17.983x) Adj Rsqr = 0.98

Fig. 8

2-Iodoethanol (AJMC-334) Pigweed Assay.
y = 16.8333/(1+17.9843x)   Adj Rsqr = 0.98

Fig. 9

2-Bromoethanol (AJMC-330) Root-knot nematode Galling
Assay. y=(3.667 −0.040x)/(1 + 0.04x) Adj Rsqr=0.88.

Fig. 10

2-iodoethanol (AJMC-334) Root-knot nematode Galling Assay. y=(5.704-0.0028x)/(1+0.0007x) Adj Rsqr=0.88.

Fig. 11

METHODS OF REDUCING PESTS BY USE OF HALOGEN SUBSTITUTED ETHANOL

REFERENCE TO RELATED APPLICATION

This application claims the benefit of U.S. Provisional Application No. 60/395,230, filed 11 Jul. 2002, which is incorporated herein by reference in its entirety.

BACKGROUND OF THE INVENTION

The present invention relates to a method for reducing pests in an object or area by applying to the object or area a pest reducing effective amount of halogen substituted ethanol (e.g., 2-iodoethanol, 2-bromoethanol, or mixtures thereof). The pests may be, for example, fungi, insects, nematodes, bacteria, weeds, or mixtures thereof. The object or area may be, for example, soil, structures, agricultural commodities, plants, or mixtures thereof.

Methyl bromide is the chemical fumigant currently utilized to control fungi, nematodes, weeds, and insects in soil that is used for the production of high value agricultural crops such as strawberries, tomatoes, peppers, orchard crops, and vine crops. In 1992, methyl bromide was implicated as an ozone-depleting compound and subsequently the production levels of methyl bromide were frozen at the 1991 production levels. Methyl bromide is targeted for a 5-year phase-out beginning in the year 2000 and will be completely phased out by the year 2005 in accordance with the Montreal Protocol. The agricultural producing states most affected by this phase-out are Florida and California, which produce the majority of the tomatoes, peppers, strawberries, cut flowers, turf/sod, tobacco, melons, pineapples, orchard crops (e.g., peaches, citrus), and vine crops (e.g., grapes) grown in the United States. The aforementioned crops are the largest consumers of methyl bromide and other EPA registered fumigants for soil fumigation purposes. As methyl bromide is phased out, current crop yields are expected to be reduced by as much as forty percent due to increased pest and weed pressure in non-fumigated soil.

There currently exist only a few EPA registered and frequently studied methyl bromide alternatives: 1,3-dichloropropene, chloropicrin, metham sodium, dazomet, methyl iodide, propargyl bromide, sodium azide, and Enzone (EPA, Methyl Bromide Web Page); these are commonly applied as mixtures of two or more of the individual compounds in order to attempt to produce a more broad spectrum product. None of these EPA registered potential alternatives are drop-in replacements for methyl bromide based on performance or economics (drop-in replacement means that methodology, equipment, production system, etc., do not have to be changed significantly and that a comparable amount of material can be used for the same targets; i.e., the material is applied at nearly the same rate and with the same equipment as methyl bromide). All the potential replacement compounds, and even methyl bromide, have worker exposure and environmental/degradation issues.

Weed control in the absence of methyl bromide is considered to be one of the areas of greatest concern to growers. None of the methyl bromide alternatives provide adequate weed control, particularly of nutsedge and grass weeds. Nutsedge is considered to be the world's worst weed due to its status as a competitor with more crops in more countries than any other weed. Purple nutsedge grows well in almost any soil type and over a wide range of soil pH, moisture, and elevation. This weed is a significant problem in field crops, horticultural crops, and turf. It is one of the few weeds that can penetrate the plastic mulch that is used in the plant bed culture to suppress weed growth. Yields of some crops can be reduced by as much as 90% as a result of competition with this weed.

Nematode, plant pathogenic fungi, and insect control in the aforementioned crops are targets of methyl bromide and any alternative to methyl bromide. Control of all plant pathogens and pests is extremely important to the production of these crops and sustained economic viability.

One goal of our research project was to evaluate new compounds to determine their efficacy as replacements for methyl bromide.

SUMMARY OF THE INVENTION

The present invention relates to a method for reducing pests in an object or area by applying to the object or area a pest reducing effective amount of halogen substituted ethanol (e.g., 2-iodoethanol, 2-bromoethanol, or mixtures thereof). The pests may be, for example, fungi, insects, nematodes, bacteria, weeds, or mixtures thereof. The object or area may be, for example, soil, structures, agricultural commodities, plants, or mixtures thereof.

DETAILED DESCRIPTION OF THE INVENTION

It has been discovered that halogen substituted ethanols (e.g., 2-bromoethanol $BrCH_2CH_2OH$, 2-iodoethanol $ICH_2CH_2OH$) may be utilized in controlling pests such as fungi, insects, nematodes, bacteria, and weeds, for example by fumigation of soil, structures, agricultural commodities (e.g., wood, grain), and plants. The compounds described herein may be employed in substantially the same manner as is customary for use of methyl bromide, chloropicrin or Telone®C-17 (DowElanco product containing 77.9 percent 1,3-dichloropropene (1,3-D) and 16.5 percent chloropicrin), Telone®C-35, Telone® II, Inline®, Metam Sodium, Nemacur®, Vydate®, and other chemical fumigants, nematicides, fungicides, herbicides, or insecticides.

Application of halogen substituted ethanols in accordance with the present invention may be effected by a number of different procedures as are currently routinely employed for soil and structural treatments with, for example, methyl bromide. Thus, for example, the compounds may be applied to the soil by tractor mounted injectors on tynes, manually in canisters and via an existing irrigation system or as a gas through lay flat tubing; furthermore, for example, the compounds may be applied by drip irrigation, shanking in, spray/rototill, or overhead sprinklers. The compounds may be dissolved in suitable solvents (e.g., water, alcohols, ethers, petroleum based solvents) and/or emulsified to assist in dispersion of the material during the treatment of, for example, soil and agricultural substances. The compounds may be heated to form a gas. Further, it is contemplated as within the scope of the invention to apply mixtures of the compounds with other fumigants, nematicides, herbicides or other agricultural chemicals, for example methyl bromide, chloropicrin, Inline® or Telone®C-17.

A wide range of application rates of the compounds may be suitable in accordance with the present invention. Those working in this field would of course be readily able to determine in an empirical manner the optimum rates of application for any given combination of plants (e.g., crops), soils, structures, and the target organisms to be killed or eliminated. The amount of compound used will be at least an effective amount to reduce pests. The term "pest reducing effective amount," as used herein, means the minimum amount of halogen substituted ethanol needed to reduce the number of pests (e.g., fungi, insects, nematodes, bacteria, or weeds) in an object or area (e.g., soil, structures, plants, or agricultural commodities such as grain or wood). As would be readily appreciated by a person skilled in the art, the delivery of the compounds can be calculated in terms of the active ingredient applied per unit area. For example, the compounds may be applied at the rate of 10–1200 pounds/acre, preferably 100–400 pounds/acre; applications of the compounds at rates substantially in excess of 1200 pounds/acre would not be expected to provide any significant advantage over applications within the ranges specified herein, but are nonetheless regarded as well within the scope of the present invention. Of course, the precise amount of the compounds needed will vary in accordance with the particular composition used; the type of area or object to be treated; the number of days of effectiveness needed; and the environment in which the area or object is located. The precise amount of the compounds can easily be determined by one skilled in the art given the teaching of this application. Other compounds may be added to the halogen substituted ethanols provided they do not substantially interfere with the intended activity of the halogen substituted ethanols; whether or not a compound interferes with activity can be determined, for example, by the procedures described below. Such other compounds include, for example, pesticides or chemicals such as chloropicrin, metam sodium, 1,3-dichloropropene(s), Plant Pro®, propylene oxide, basamid, alkyl iodides), generally in ratios in the range of 1:10 to 10:1, in order to enhance efficacy or improve use economics.

A wide range of timing of application of the compounds may be suitable in accordance with the present invention. Those working in this field would of course be readily able to determine in an empirical manner the optimum timing of application for any given combination of crops, soils, structures, and the target organisms to be killed or eliminated. For example, the timing of application may be pre- or post-bedding, pre-transplant, pre-seed, or pre-plant. The compounds may be applied to the soil during the post-planting and/or post-emergence cropping period in levels sufficient to control a target pest or pathogen without hurting the crop (e.g., grapes, peaches, bananas, ornamentals, coffee, etc.). The compounds may also be used on corms, bulbs, or tubers prior to planting and after planting. Furthermore, the compounds may be used as pre- or post-emergent herbicides during or before the cropping season.

Those working in this field would of course be readily able to determine in an empirical manner which organisms may be killed or eliminated by the compounds. Plant pathogenic organisms successfully controlled or eliminated by treatments in accordance with the present invention include, but are not limited to, nematodes, fungi, weeds, bacteria, and insects; for example, nematodes (e.g. *Meloidogyne* spp. (Root Knot), *Xiphinema* spp. (Dagger), *Pratylenchus* (Lesion), *Longidorus* spp. (Needle), *Paratylenchus* spp. (Pin), *Rotylenchulus* spp. (Reniform), *Helicotylenchus* spp. (Spiral), *Hoplolaimus* spp. (Lance), *Paratrichodorus* spp. (Stubby Root), *Tylenchorhynchus* spp. (Stunt), *Radopholus* spp. (Burrowing), *Anguina* spp. (Seed Gall), *Aphelenchoides* spp. (Folair), *Bursaphelenchus* spp. (pinewood), *Ditylenchus* spp. (Stem, Bulb, and Potato Rot), *Trichchodorus* spp., *Globodera* spp. (Potato Cyst), *Hemicycliophora* spp. (Sheath), *Heterodera* spp. (Cyst), *Dolichodorus* spp. (Awl), *Criconemoides* spp. (ring), *Belonolaimus* spp. (Sting), *Tylenchulus semipenetrans* (Citrus)), plant pathogenic fungi (e.g., *Cylindrocarpon* spp., *Fusarium* spp., *Phoma* spp., *Phytophthora* spp., *Pythium* spp., *Rhizoctonia* spp., *Sclerotinia* spp., *Verticillium* spp.), plant pathogenic bacteria (e.g., *Pseudomonas* spp.), and insects (e.g. wireworms, thrips, beetle larva, grubs). Particular plant pathogens and nematodes controlled or eliminated by application of the compounds include, but are not limited to, the following: root rot pathogens (e.g., *Phytophthora* spp;, *Pythium* spp., *Rhizoctonia* spp., *Fusarium* spp.); vascular wilt pathogens (e.g., *Verticillium* spp., *Fusarium* spp.); root knot and extoparasitic nematodes (e.g., *Meloidogyne* spp., *Pratylenchus* spp., *Rotylenchus* spp., *Tylenchorrhynchus* spp., *Xiphinema* spp.); root lesion nematodes (e.g., *Pratylenchus vulnus*); ring nematodes (e.g., *Circonemella xenoplax*); stubby root nematodes (e.g., *Paratiichodorus* spp.); stem and bulb nematodes (e.g., *Ditylenchus dipsaci*); cyst nematodes (e.g., *Heterodera schachtii*); citrus nematodes (e.g., *Tylenchulus semipenetrans*); and burrowing nematodes (e.g., *Radopholus similus*). Among the types of weeds controlled or eliminated by application of the compounds include, but are not limited to, the following: purple nutsedge (*Cyperus rotundus*); smooth pigweed (*Amaranthus hybridus*); barnyard grass (*Echinocola crus-galli*); cheeseweed (*Malva* spp.); field bindweed (*Convolvulus arvensis*); annual bluegrass (*Poa annua*); bermuda grass; crab grass; foxtail; purs lane; and witchweed. Particular insects controlled or eliminated by application of the compounds include, but are not limited to, the following: fungal gnat larvae, soil mealy bugs, phylloxera, ants, termites, and animal parasites.

The compounds may be applied to a wide variety of agricultural plants, for example, tomatoes, peppers, carrots, potatoes, strawberries, melons, pineapples, tobacco, bananas, ornamentals, cut flowers, turf/sod, tobacco, trees/seedlings, coffee, orchard crops (e.g., peaches, citrus), and vine crops (e.g., grapes).

The following examples are intended only to further illustrate the invention and are not intended to limit the scope of the invention as defined by the claims.

EXAMPLES

Materials and Methods:

*Fusarium* Tetrazolium Assay: The evaluation of fungicidal activity was performed using a modified colorimetric assay (Mace, M. E., et al., Pesticide Biochemistry and Physiology, 38: 57–59 (1990)). Each candidate compound was tested using a suspension of *Fusarium oxysporum* f. sp. *lycopersici* (isolate FP-7) spores harvested from 10-day old petri plates using a 0.05% stock solution of Triton X-100 (referred to as FT stock). Harvested spores were suspended in Czapek-Dox Broth (CDB), prepared according to label instructions, at a ratio of 1:5 CDB:FT. The suspension was then standardized using a Beckman spectrophotometer (430 nm) which had been calibrated using a CDB blank. Compounds were then added to aliquots of the suspension to achieve active ingredient concentrations ranging from 0 ppm (untreated control) to 2000 ppm. Suspensions were incubated for 24 hr at 28° C. A 10% stock solution of MTT ((3-4,5-dimethylthiazole-2-yl)-2,5-diphenyl-2-2H-tetrazolium bromide) was then added to each aliquot; MTT is a vital stain that is commonly used to show if an organism is alive based on a color change). The suspensions were allowed to incubate for 4 hr, and then pelleted, drained, rinsed, and treated with 95% ethanol. The color change, which correlates with spore viability, was assessed using a Beckman spectrophotometer (570 nm) calibrated with 95% ethanol. Benlate® (benomyl) was used as an industry standard control. Each treatment was replicated six times and the assay for each compound was repeated. Regression analysis was performed using Sigma Plot 2000.

Herbicide Screen: Each compound was tested on seeds of smooth pigweed (*Amaranthus hybridus*) and barnyard grass (*Echinocloa crus-galli*), and on tubers of purple nutsedge (*Cyperus rotundus*), by exposing seeds or tubers to a specific concentration of the test compound. Seeds were surface sterilized (by rinsing in 2% bleach solution for 90 seconds followed by two rinses with sterile water) and 20 seeds placed on sterile filter paper (Whatman #5) in a 10-cm petri plate for each of six replicates for each weed species tested. Twenty ml of compound of concentrations ranging from 0 ppm (sterile water control) to 2000 ppm was added to the petri dishes. Plates were stored at 30° C. in an dark incubator. Seed germination was monitored at 24 hr intervals for 30 days. Petri plate bioassays were repeated twice for each compound. Field collected purple nutsedge tubers were placed in 500 g of field soil with soil moisture adjusted to 5%. Five nutsedge tubers were planted in each 10 cm pot at a depth of 2.5 cm. Six replicate pots of each concentration, ranging from 0 ppm (water control) to 2000 ppm, were treated using 100 ml as a soil drench. Pots were tarped with co-extruded black-on-white polyethylene mulch for 7 days. After the tarps were removed, the number of emerged nutsedge shoots was recorded on a weekly basis for 60 days.

Nematicide Screen: Efficacy as a nematicide was evaluated by infesting field soil with a standardized quantity of root-knot nematode eggs (*Meliodogyne incognita*). Soil was partitioned into 10 cm pots containing 500 g of soil each with soil moisture adjusted to 5%. Pots were treated with compounds ranging from 0 ppm to 2000 ppm of active ingredient in a 100-ml soil drench. Six replicate pots of each concentration were treated and tarped with co-extruded black-on-white polyethylene mulch for 14 days. After tarps were removed, a single tomato seedling was transplanted into each pot. Seedlings were removed 30 days later and assessed for root galling, root fresh weight, root dry weight, and number of eggs produced per gram of root tissue.

The above tests may be used with other nematodes, fungi, weeds, bacteria, and insects.

Figure 1:
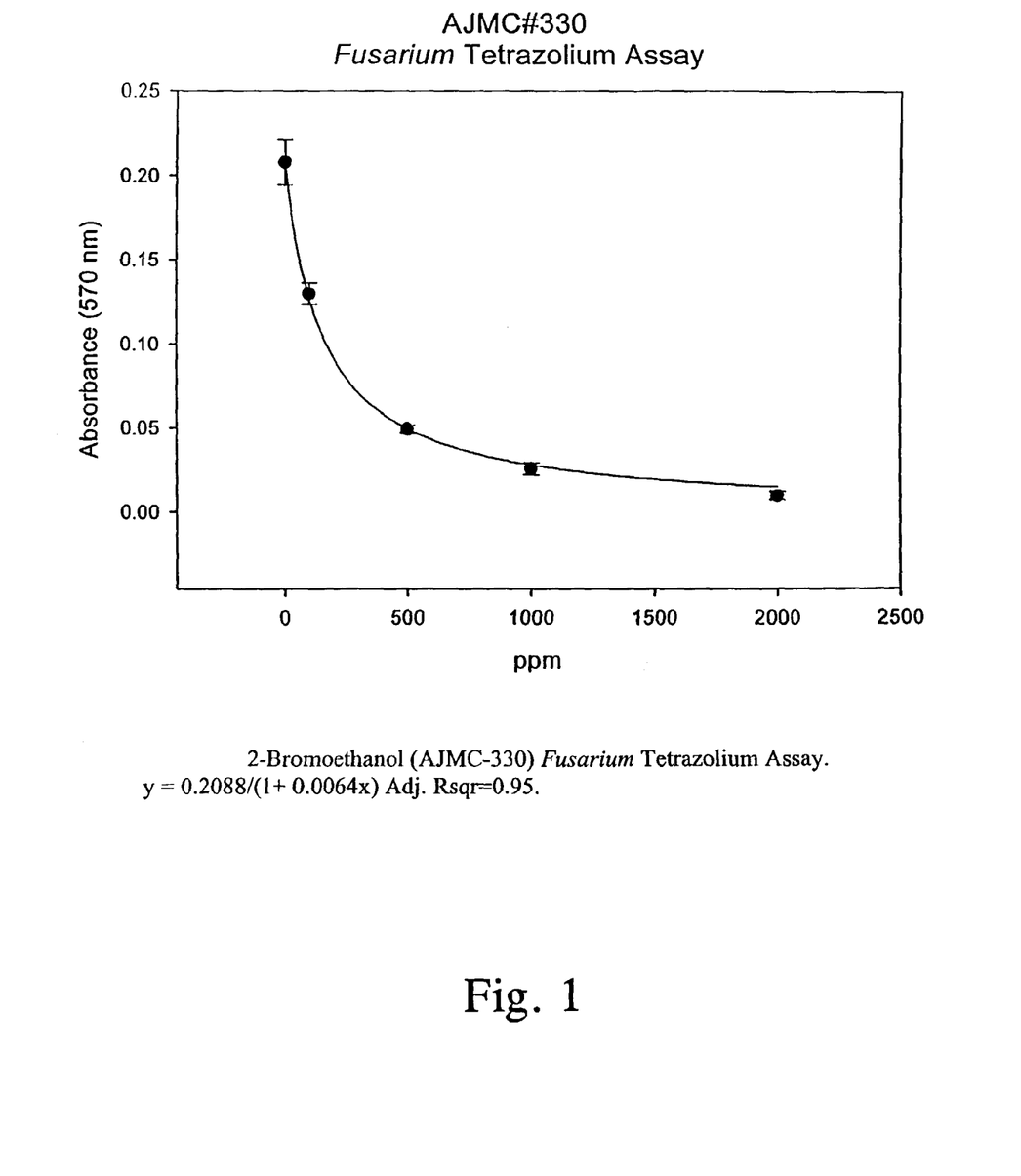
FIG. 1 shows results of testing 2-bromoethanol in a *Fusarium* tetrazolium assay.
Figure 2:
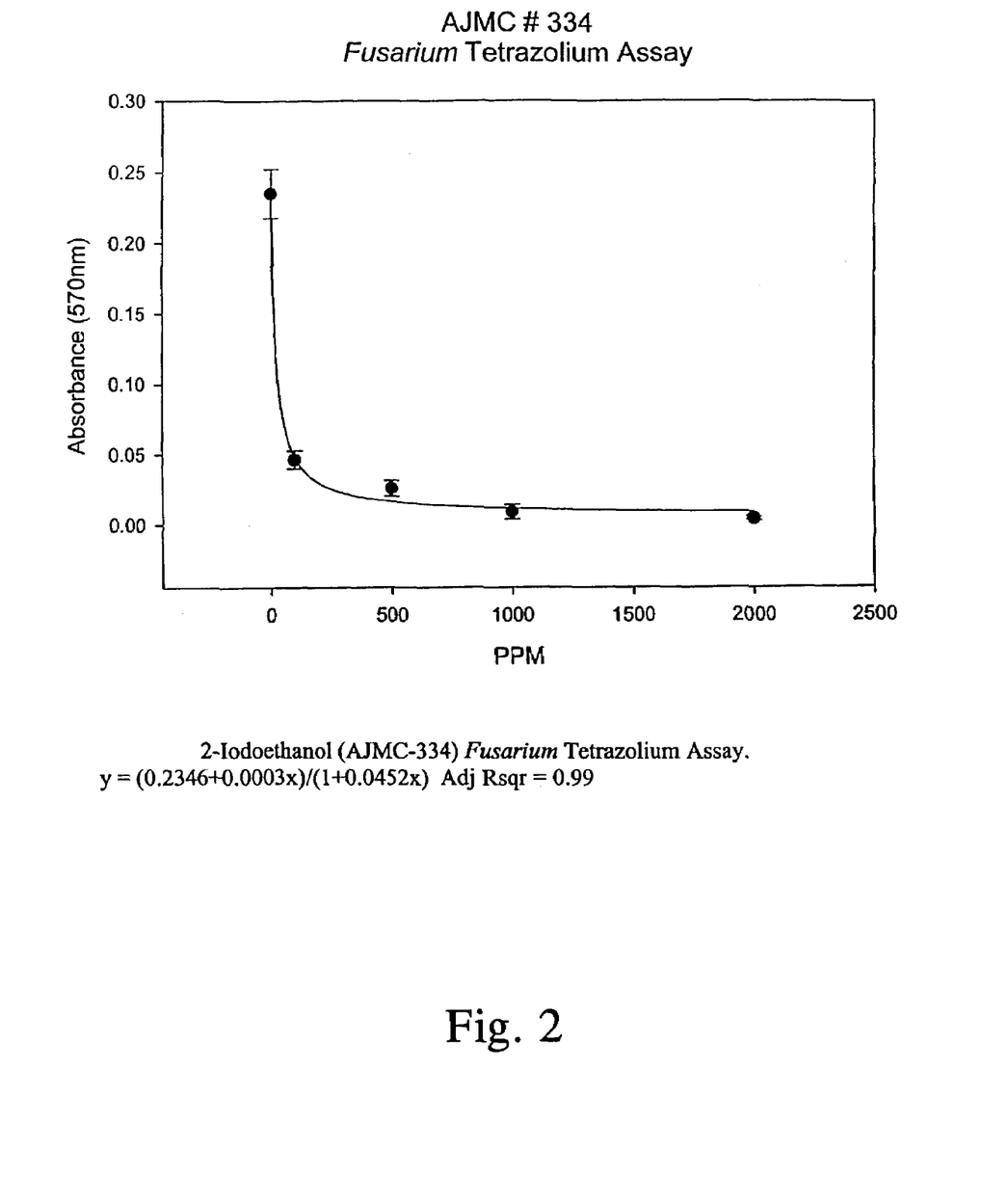
FIG. 2 shows results of testing 2-iodoethanol in a *Fusarium* tetrazolium assay.
Figure 3:
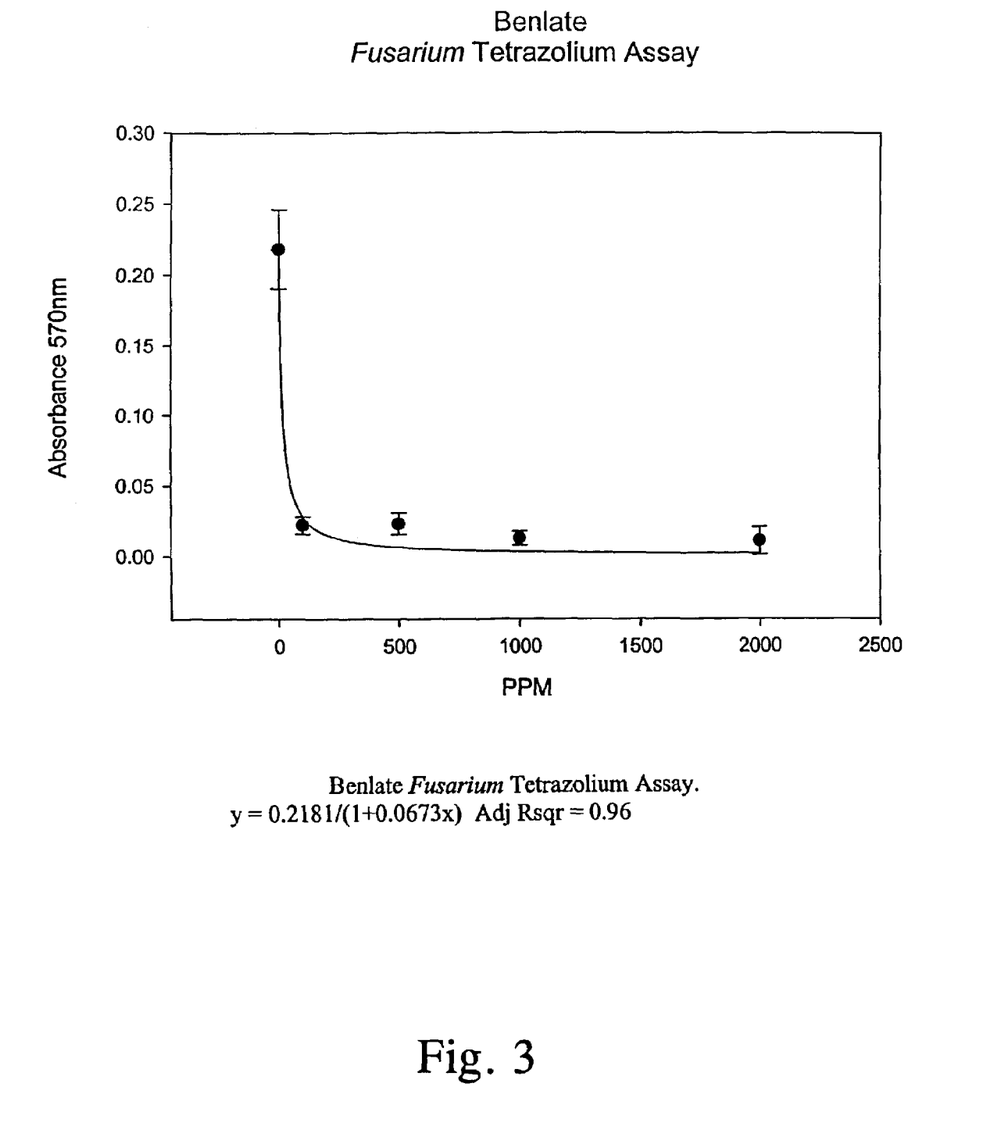
FIG. 3 shows results of testing Benlate® control in a *Fusarium* tetrazolium assay.

Results and Discussion:

*Fusarium* Tetrazolium Assay: Results from these assays appear in FIGS. 1–3 wherein the graphs are plots of the ppm versus resulting absorbance at 570 nm after 24 hours of exposure to the compound. The assay was based on a color change produced with a vital stain on living tissue (i.e., the lower the absorbance, the fewer viable cells). In this test, 2-iodoethanol was comparable to the Benlate® control. 2-bromoethanol was effective at reducing cell viability to levels achieved with Benlate® (100 ppm) at concentrations between 500 and 1000 ppm. 2-iodoethanol was effective at the 100–500 ppm range. Thus both compounds have excellent fungicidal activity.

Figure 4:
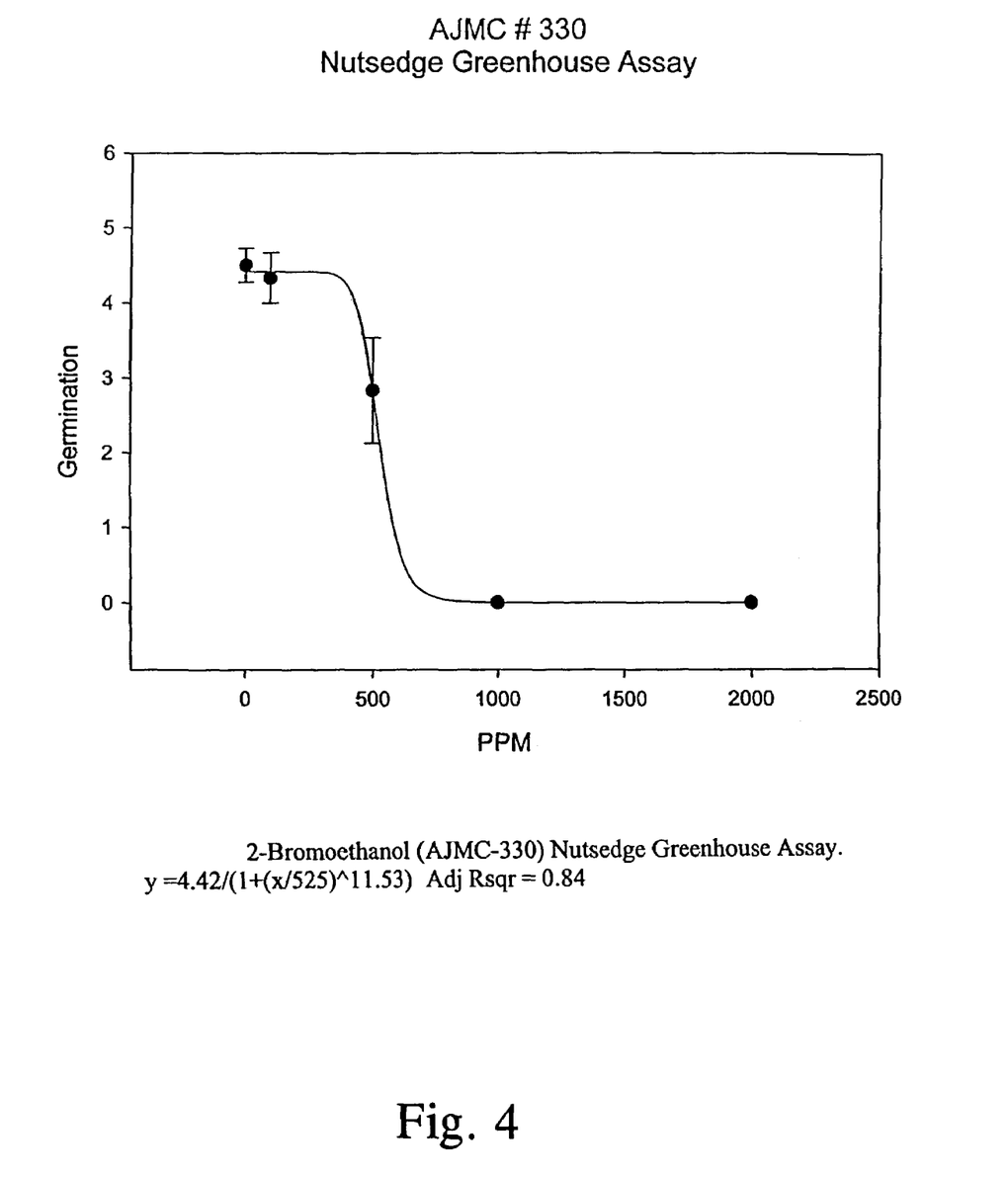
FIG. 4 shows results of testing 2-bromoethanol in a nutsedge greenhouse assay.
Figure 5:
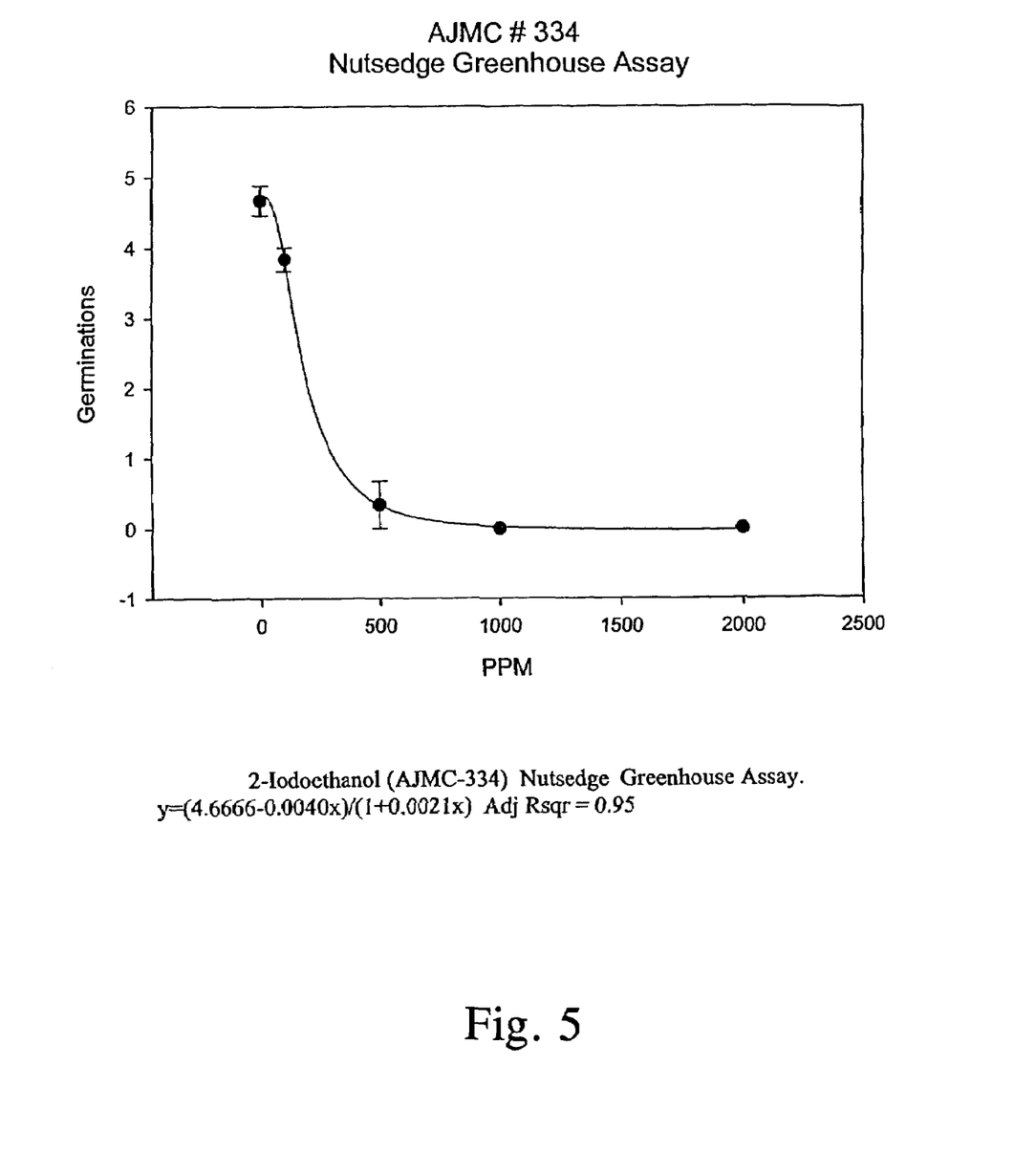
FIG. 5 shows results of testing 2-iodoethanol in a nutsedge greenhouse assay.
Figure 6:
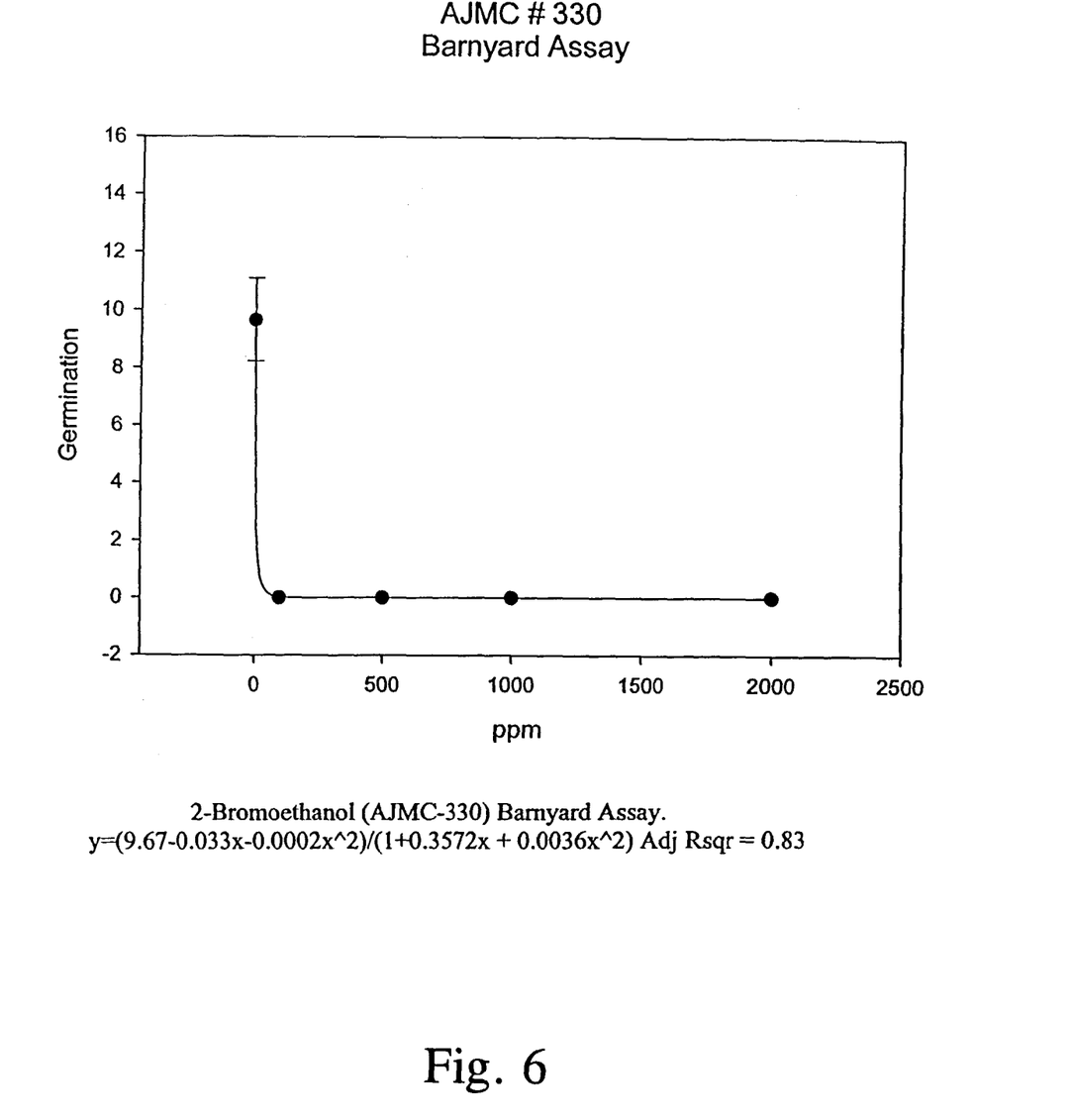
FIG. 6 shows results of testing 2-bromoethanol in a barnyard grass assay.
Figure 7:
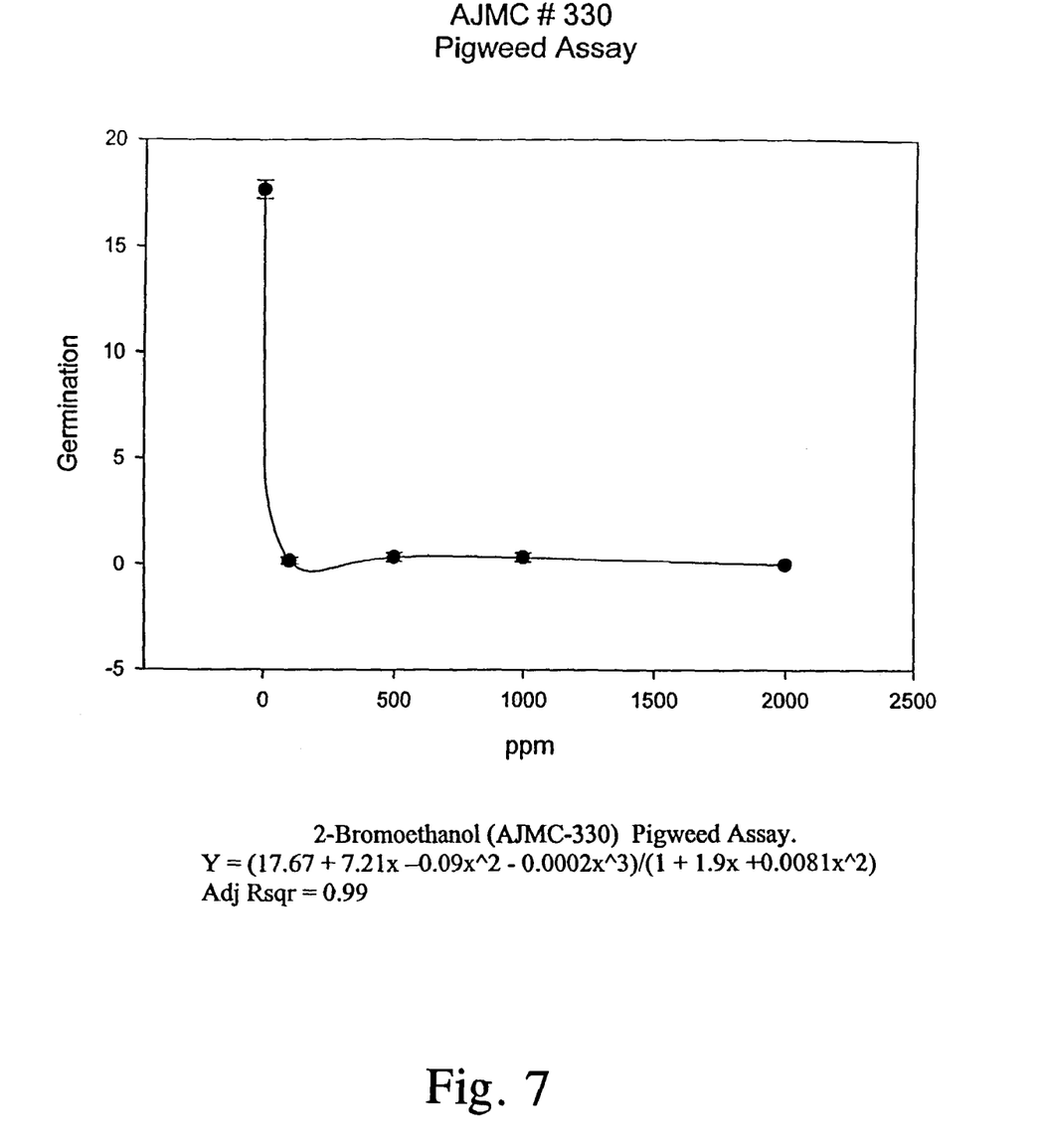
FIG. 7 shows results of testing 2-bromoethanol in a smooth pigweed assay.
Figure 8:
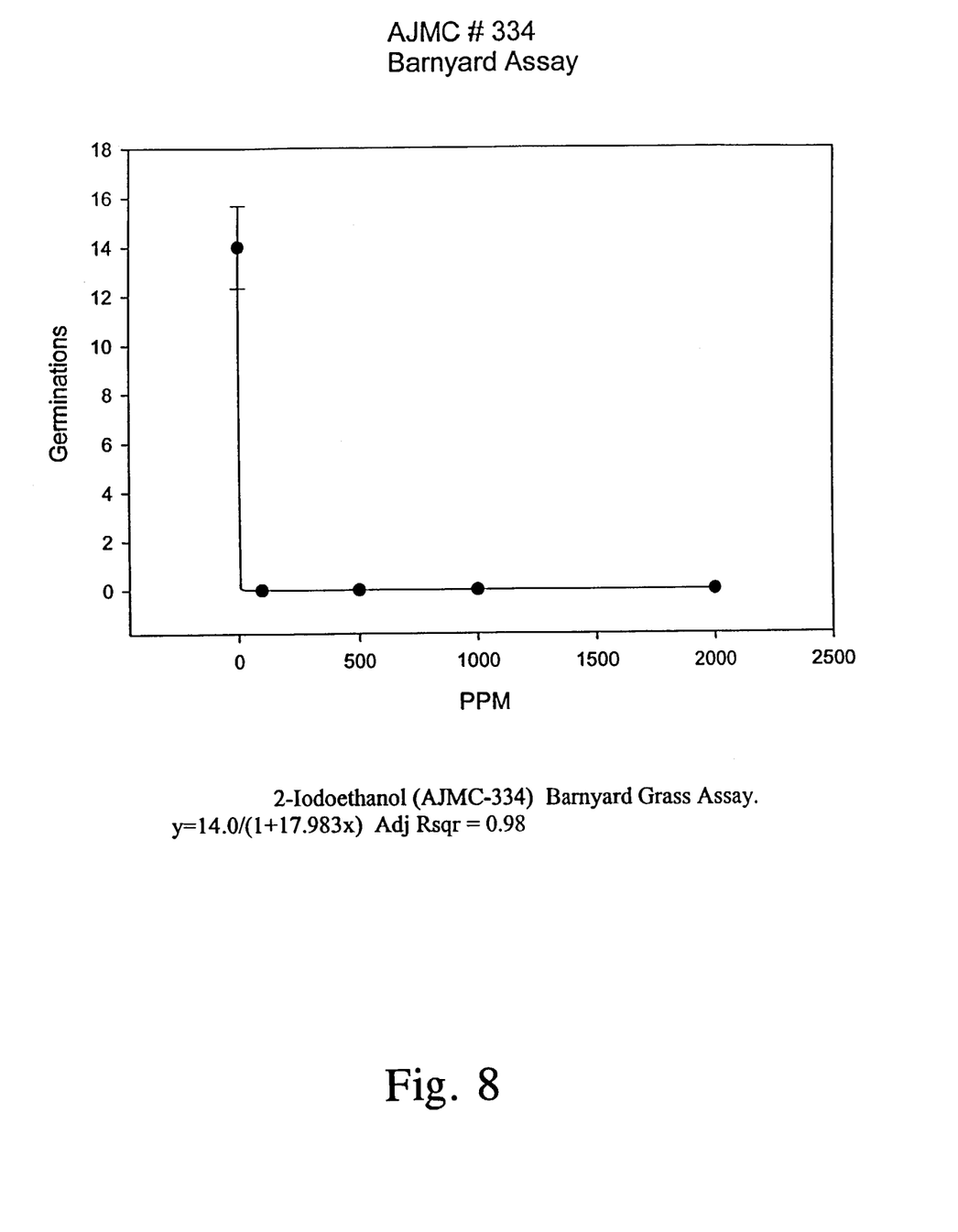
FIG. 8 shows results of testing 2-iodoethanol in a barnyard grass assay.
Figure 9:
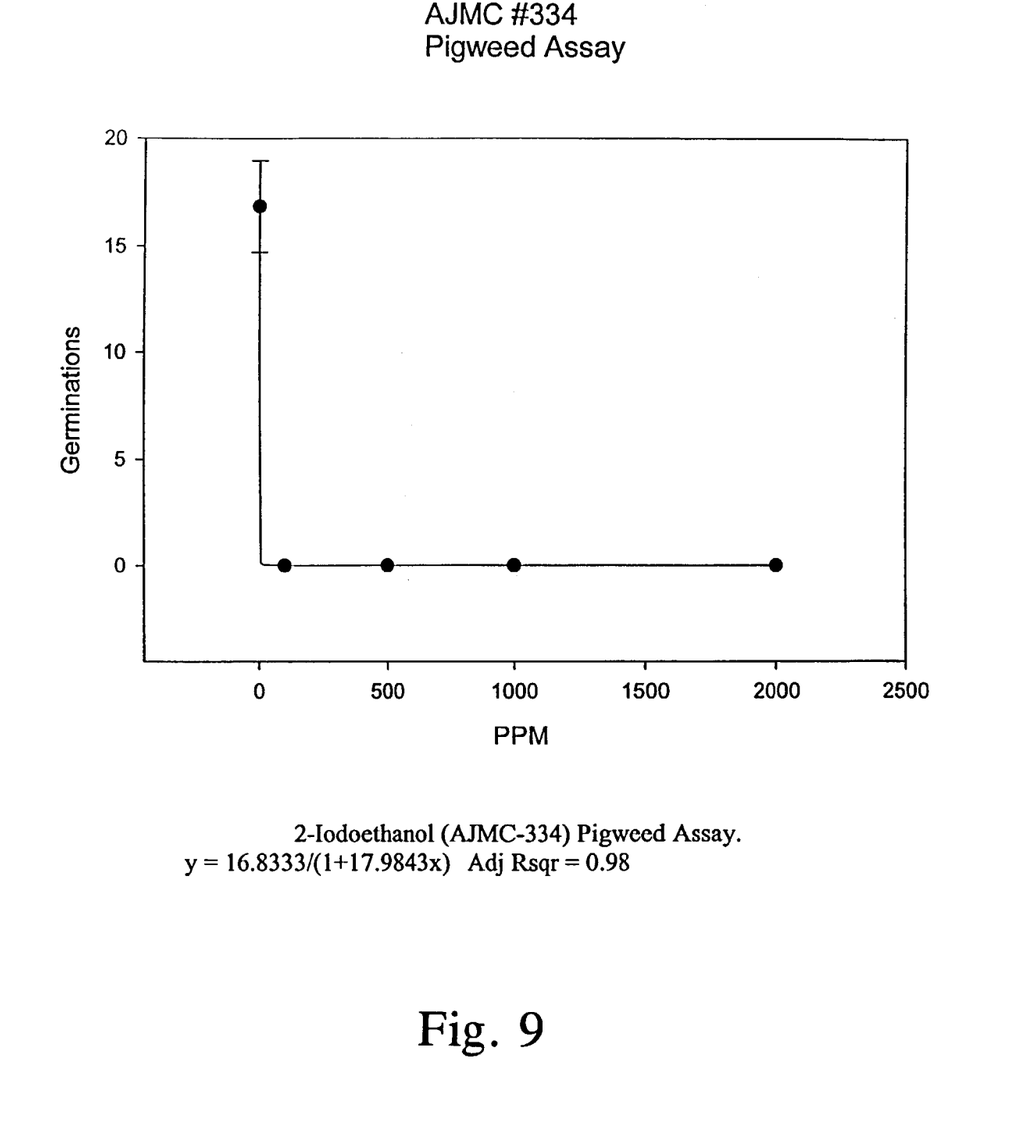
FIG. 9 shows results of testing 2-iodoethanol in a smooth pigweed assay.

Herbicide Screen: 2-bromoethanol was effective in eliminating the germination of nutsedge at the 1000 ppm level and above. This rate was equivalent to 200 ppm soil applied equivalent. Germination was reduced to approximately 50% at the 500 ppm level (FIG. 4). 2-iodoethanol eliminated nutsedge germination at the 500 ppm level and above (FIG. 5). Germination of barnyard grass and pigweed seeds was eliminated at all ppm levels tested (FIGS. 6–9) of both compounds, 2-bromoethanol and 2-iodoethanol; it is expected that lower quantities of active ingredient (<100 ppm) will also be effective.

Figure 10:
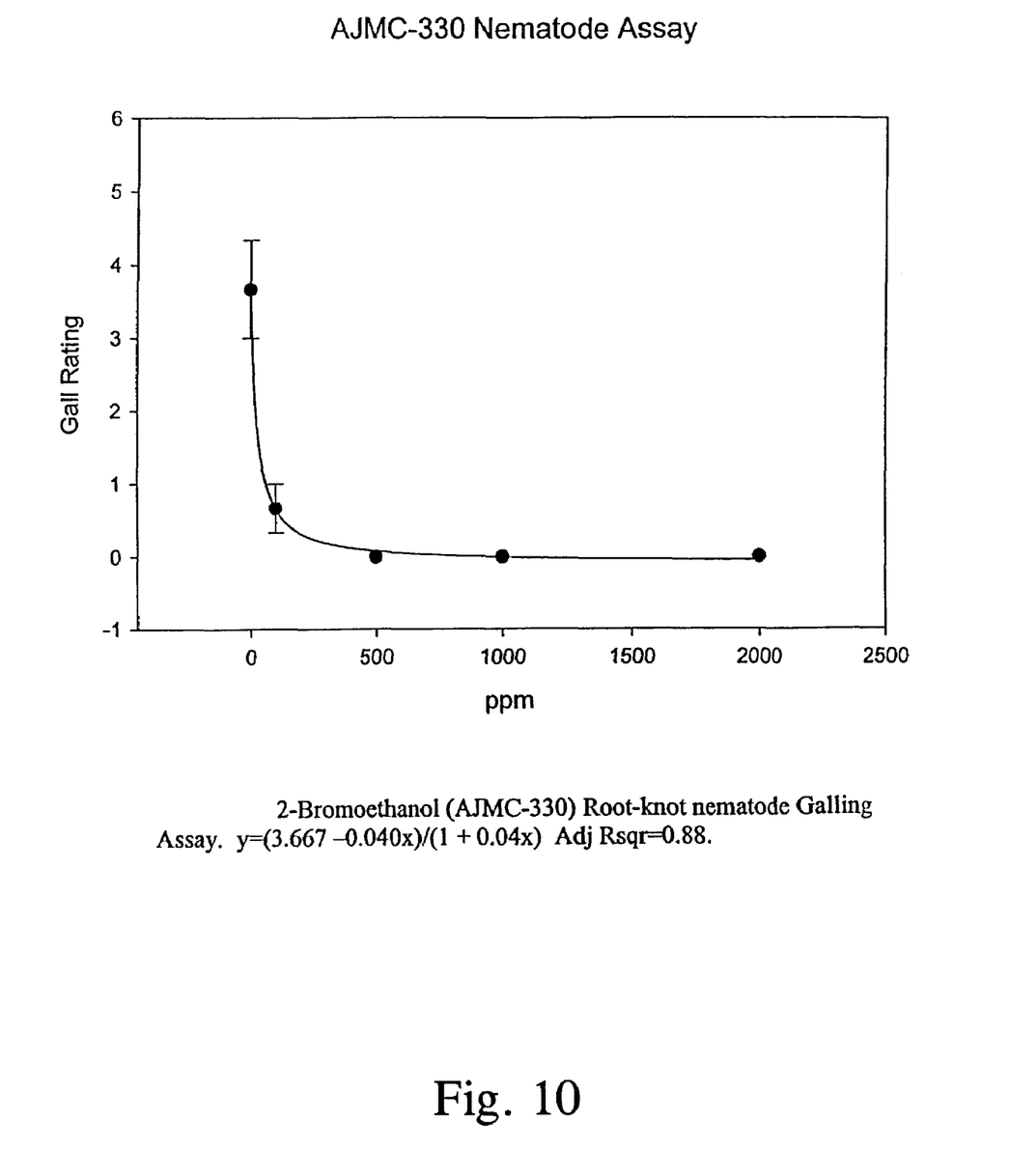
FIG. 10 shows results of testing 2-bromoethanol in a root-knot nematode galling assay.
Figure 11:
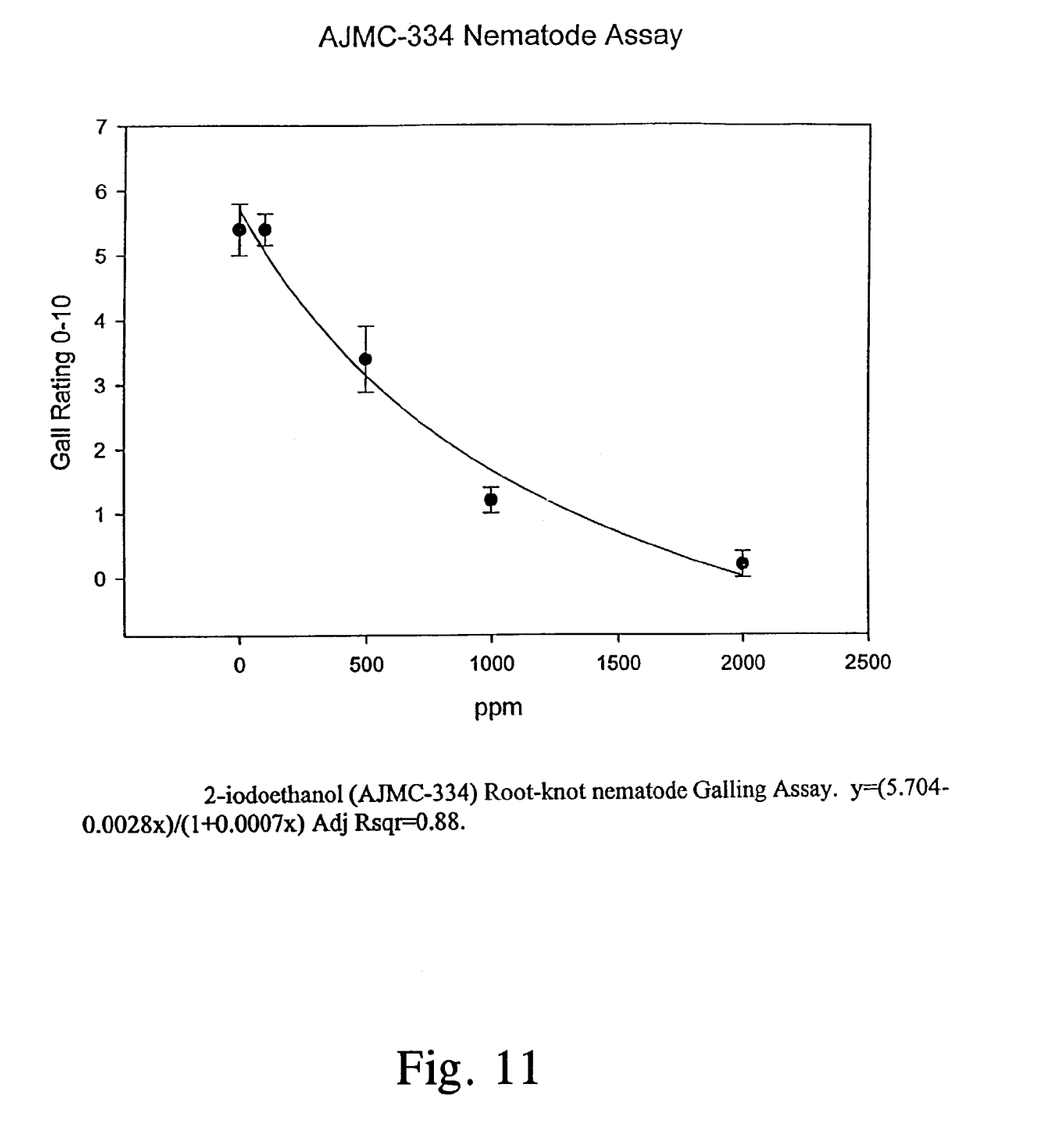
FIG. 11 shows results of testing 2-iodoethanol in a root-knot nematode galling assay.

Nematode Assay: Data on root gall severity on tomato for 2-bromoethanol appears in FIG. 10. Only the untreated control showed galling of any kind. Data on root gall severity on tomato for 2-iodoethanol appears in FIG. 11; galling decreases with increased concentration of 2-iodoethanol.

Field Example (to evaluate the growth and fruit yield and pathogen and weed control of preplant drip fumigation with 2-bromoethanol):

Materials and Methods:

Site description and treatment application: Field studies were conducted in Salinas and Watsonville, Calif. from September through July. Both sites were located in a major strawberry production district on the central coast of California. The soil in both locations had not been fumigated for at least 10 years prior to initiation of this research. The soil at Salinas was classified as a Chualar sandy loam (fine-loamy, mixed, thermic, Typic Argixerolls) with a pH of 6.5 and organic matter content of 0.7%. The soil in Watsonville was classified as an Elder sandy loam (coarse-loamy, mixed, thermic, Cumulic Haploxerolls) with a pH of 6.1 and organic matter content of 0.6%. Commercial cultural practices for the area were followed. The soil was tilled and beds were formed in both locations at 132 cm center-to-center spacing (76 cm wide and 30 cm high). Slow release fertilizer (27N-10P-12K) was applied to the beds at the rate of 400 kg·ha$^{-1}$. The drip irrigation system consisted of two drip tapes (Netafim Streamline 60, Netafim, Fresno, Calif.), with emitters spaced 30 cm apart and an emitter flow rate of 0.87 L min$^{-1}$ at 70 KPa, placed 8 cm (in Watsonville) or 13 cm (in Salinas) from the bed center at a soil depth ranging from 2 to 5 cm. Preplant fumigation was approximately four weeks before planting. The treatments were arranged in a randomized complete block design with three replicates in Watsonville and four in Salinas. Plots were one bed wide by 10 m long at Watsonville and one bed wide by 33 m long at Salinas. At the time of fumigation, the average daily soil temperature within the raised bed ranged between 16° to 20°

C., and the average soil moisture content was less than 85% of field capacity (soil matric potentials ranged between −7.5 and −8.5 KPa).

At both locations, MB:CP (methyl bromide:chloropicrin) (67:33 w/w) was shank injected 25 to 30 cm deep with two chisels spaced 35 cm apart into soil beds that were immediately covered with green or brown high-density polyethylene mulch (0.03-mm thickness). Injection rates of MB:CP were 400 and 350 pound per acre in Watsonville and Salinas, respectively. 2-bromoethanol (neat formulation (95% pure)) was applied through the drip irrigation system into soil beds covered with polyethylene mulch. 2-bromoethanol was injected at a rate of 400 pound per acre into the irrigation water (50 L water per m$^2$) throughout the irrigation period following procedures described by Ajwa et al. (Ajwa, H., and T. Trout, Strawberry growth and yield with three years of drip fumigation, 2000 Annual International Research Conference on Methyl Bromide Alternatives and Emissions Reductions, Orlando, Fla., Abstract 25; Ajwa, H., T. Trout, S. D. Nelson, and M. Schutter, Drip fumigation: water and fumigant distribution in soil, 2001 Annual International Research Conference on Methyl Bromide Alternatives and Emissions Reductions, San Diego, Calif., Abstract 50). Strawberries (*Fragaria X ananassa* Duchesne) were planted four to five weeks after fumigation. Overhead sprinklers were used for up to four weeks to establish the strawberry transplants.

Fruit yield and pest control assessments: Fruit was harvested at least once every week throughout the production season (early April to September) and graded into marketable (fresh market grade) and non-marketable (processing grade). The percentage of infested (wilting and dead) plants was recorded from all plants in the bed five and eight months after planting. Randomly selected infested plants and the surrounding soil were sampled to identify the dominant plant pathogens. Soil and plant tissue samples were assayed for *Verticillium dahliae* Kleb., *Pythium* spp., and *Rhizoctonia solani*. Weeds were assessed by weighing the total biomass of the native weed population in the raised soil beds. Weeds were uprooted and shaken to remove residual soil from the roots and then weighed to measure weed biomass.

The above tests may be used with other nematodes, fungi, weeds, bacteria, and insects.

Results and Discussion:

Plant Vigor and Fruit Yield: At the Watsonville site, yields from the untreated control were about 60% of the yields from the MB:CP plots. However, drip applied 2-bromoethanol produced >95% of the MB:CP fumigation. Although wilt at the Salinas site was not significant and the soil had medium to low infestation with *Pythium* spp., yields from the untreated control were considerably less than the yields from the MB:CP plots. Also, drip applied 2-bromoethanol produced more fruits (115%) relative to MB:CP fumigation.

Total weed biomass from the experiments in Watsonville and Salinas plots are presented in Tables 1 and 2, respectively.

In Watsonville, the soil was greatly infested with *Verticillium dahliea* (10 to 60 viable microscerotia g$^{-1}$ soil), and the percentage of dead strawberry plants was greater in the untreated control than 2-bromoethanol or MB:CP treatments. The MB:CP and 2-bromoethanol treatments reduced the population of *Verticillium dahliea* by 91% and 74%, respectively.

The number of pathogen infested plants throughout the growing season in Salinas was small in any of the treatments, and the percentage of dead plants was not significantly different (P<0.05) between MB:CP or 2-bromoethanol treatments. The predominant pathogenic fungi in this soil were *Pythium* spp. (10 to 30 propagules g$^{-1}$ soil) and *Rhizoctonia solani* (5 to 10 colonies g$^{-1}$ soil). In Salinas, 2-bromoethanol was similar to MB:CP in controlling *Pythium* spp and *Rhizoctonia solani*; they reduced the populations by more that 90%.

Fumigant efficacy on native weeds: The weed viability in the 2-bromoethanol plots was similar to viability in the MB:CP plots (Tables 1 and 2). At Watsonville, 2-bromoethanol provided control of most weeds like BM:CP. At Salinas, both 2-bromoethanol and MB:CP controlled more than 50% of total weeds.

In summary, results from our studies provide evidence that 2-bromoethanol is a viable alternative to MB shank fumigation. Due to its properties, 2-bromoethanol should be delivered directly to the target zone. The excellent results obtained with drip fumigation of 2-bromoethanol may be due to the good distribution in soil and greater retention time. We expect similar efficacy by shank injected 2-bromoethanol if proper injection equipment are used.

All of the references cited herein are incorporated by reference in their entirety. Also incorporated by reference in their entirety are the following U.S. Pat. Nos. 5,753,183; 5,698,592; 5,447,945; 4,726,144

Thus, in view of the above, the present invention concerns (in part) the following:

A method for reducing pests in an object or area, said method comprising (or consisting essentially of or consisting of) applying to the object or area a pest reducing effective amount of halogen substituted ethanol.

The above method, wherein the pests are fungi or insects or nematodes or bacteria or weeds or mixtures thereof.

The above method, wherein the pests are at least one member selected from the group consisting of fungi, insects, nematodes, bacteria, weeds, and mixtures thereof.

The above method, wherein the pests are fungi (e.g., *Fusarium* spp.).

The above method, wherein the pests are insects.

The above method, wherein the pests are nematodes (e.g., *Meliodogyne incognita*).

The above method, wherein the pests are bacteria.

The above method, wherein the pests are weeds (e.g., *Amaranthus hybridus, Echinocloa crus-galli, Cyperus rotundus*, or mixtures thereof).

The above method, wherein the object or area is soil, structures, agricultural commodities, plants, or mixtures thereof.

The above method, wherein the object or area is at least one member selected from the group consisting of soil, structures, agricultural commodities, plants, and mixtures thereof.

The above method, wherein the object or area is soil.

The above method, wherein the object or area is a structure.

The above method, wherein the object or area is an agricultural commoditie.

The above method, wherein the object or area is a plant.

The above method according, wherein the pest reducing effective amount is about 10 to about 1200 pounds/acre.

The above method according, wherein the pest reducing effective amount is about 100 to about 400 pounds/acre.

The above method, wherein the halogen substituted ethanol is 2-bromoethanol, 2-iodoethanol, or mixtures thereof.

The above method, wherein the halogen substituted ethanol is 2-bromoethanol.

The above method, wherein the halogen substituted ethanol is 2-iodoethanol.

The above method, wherein the halogen substituted ethanol is a mixture of 2-bromoethanol and 2-iodoethanol.

A method for soil fumigation, said method comprising (or consisting essentially of or consisting of) applying to soil a pest reducing effective amount of halogen substituted ethanol.

A method for structure fumigation, said method comprising (or consisting essentially of or consisting of) applying to a structure a pest reducing effective amount of halogen substituted ethanol.

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Total weed biomass (gram/m$^2$) in Watsonville plots.

| Treatment | Rate acres$^{-1}$ | Common chickweed | Corn spurry | Annual Bluegrass | Annual sowthistle | Redstem filaree | Southern brassbuttons | Little mallow | Other weeds | Total[a] |
|---|---|---|---|---|---|---|---|---|---|---|
| MB:CP | 400 lbs | 0.0 | 0.0 | 1.2 | 0.0 | 2.9 | 0.3 | 3.0 | 1.8 | 9.2a |
| 2-bromoethanol | 400 lbs | 1.6 | 1.1 | 5.9 | 0.0 | 0.3 | 1.0 | 0.2 | 3.6 | 13.7a |
| Untreated | 0 | 7.3 | 6.7 | 11.4 | 2.8 | 0.1 | 2.9 | 0.1 | 8.2 | 39.5b |

[a]Percentages followed by the same letter in the column are not significantly different at $P < 0.05$

TABLE 2

Total weed biomass (gram/m$^2$) in Salinas plots.

| Treatment | Rate acres$^{-1}$ | Shepherd-spurse | Henbet | Commong roundsel | Little mallow | Other weeds | Total[a] |
|---|---|---|---|---|---|---|---|
| MB:CP | 400 lbs | 4.0 | 1.7 | 0.0 | 16.5 | 20.2 | 42.4a |
| 2-bromoetbanol | 400 lbs | 11.3 | 9.4 | 0.3 | 4.2 | 21.5 | 46.7a |
| Untreated | 0 | 32.6 | 28.5 | 2.0 | 6.1 | 30.1 | 99.3b |

[a]Percentages followed by the same letter in the column are not significantly different at $P < 0.05$

We claim:

1. A method for reducing pests in an object or area, said method comprising applying to said object or area a pest reducing effective amount of halogen substituted ethanol, wherein said halogen substituted ethanol is selected from the group consisting of 2-bromoethanol, 2-iodoethanol, and mixtures thereof, and wherein said pests are selected from the group consisting of insects, nematodes, weeds, and mixtures thereof.

2. The method according to claim 1, wherein said pests are insects.

3. The method according to claim 1, wherein said pests are nematodes.

4. The method according to claim 3, wherein said nematodes are *Meliodogyne incognita*.

5. The method according to claim 1, wherein said pests are weeds.

6. The method according to claim 5, wherein said weeds are selected from the group consisting of *Amaranthus hybridus, Echinocloa crus-galli, Cyperus rotundus*, and mixtures thereof.

7. The method according to claim 1, wherein said object or area is selected from the group consisting of soil, structures, agricultural commodities, plants, and mixtures thereof.

8. The method according to 7, wherein said object or area is soil.

9. The method according to claim 1, wherein said pest reducing effective amount is about 40 to about 1200 pounds/acre.

10. The method according to claim 1, wherein said halogen substituted ethanol is 2-bromoethanol.

11. The method according to claim 1, wherein said halogen substituted ethanol is 2-iodoethanol.

12. The method according to claim 1, wherein said halogen substituted ethanol is a mixture of 2-bromoethanol and 2-iodoethanol.

13. A method for reducing pests in an object or area, said method consisting essentially of applying to said object or area a pest reducing effective amount of halogen substituted ethanol, wherein said halogen substituted ethanol is selected from the group consisting of 2-bromoethanol, 2-iodoethanol, and mixtures thereof.

14. The method according to claim 13, wherein said pests are selected from the group consisting of fungi, insects, nematodes, bacteria, weeds, and mixtures thereof.

15. The method according to claim 14, wherein said pests are fungi.

16. The method according to claim 15, wherein said fungi are *Fusarium* spp.

17. The method according to claim 14, wherein said pests are insects.

18. The method according to claim 14, wherein said pests are nematodes.

19. The method according to claim 18, wherein said nematodes are *Meliodogyne incognita*.

20. The method according to claim 14, wherein said pests are bacteria.

21. The method according to claim 14, wherein said pests are weeds.

22. The method according to claim 21, wherein said weeds are selected from the group consisting of *Amaranthus hybridus, Echinocloa crus-galli, Cyperus rotundus*, and mixtures thereof.

23. The method according to claim 13, wherein said object or area is selected from the group consisting of soil, structures, agricultural commodities, plants, and mixtures thereof.

24. The method according to claim 23, wherein said object or area is soil.

25. The method according to claim 13, wherein said pest reducing effective amount is about 40 to about 1200 pounds/acre.

26. The method according to claim 13, wherein said halogen substituted ethanol is 2-bromoethanol.

27. The method according to claim 13, wherein said halogen substituted ethanol is 2-iodoethanol.

28. The method according to claim 13, wherein said halogen substituted ethanol is a mixture of 2-bromoethanol and 2-iodoethanol.

29. A method for reducing pests in an object or area, said method comprising applying to said object or area a pest reducing effective amount of 2-iodoethanol.

* * * * *